US008045848B2

(12) United States Patent
Wortley

(10) Patent No.: US 8,045,848 B2
(45) Date of Patent: Oct. 25, 2011

(54) BABYCARE HEATING APPARATUS

(75) Inventor: Mark John Wortley, Sudbury (GB)

(73) Assignee: Koninklijke Philips Electronics N.V., Eindhoven (NL)

( * ) Notice: Subject to any disclaimer, the term of this patent is extended or adjusted under 35 U.S.C. 154(b) by 1080 days.

(21) Appl. No.: 10/556,142

(22) PCT Filed: Apr. 29, 2004

(86) PCT No.: PCT/EP2004/050653
§ 371 (c)(1),
(2), (4) Date: Apr. 28, 2008

(87) PCT Pub. No.: WO2004/098659
PCT Pub. Date: Nov. 18, 2004

(65) Prior Publication Data
US 2008/0199164 A1    Aug. 21, 2008

(30) Foreign Application Priority Data
May 9, 2003    (GB) .................................. 0310711.7

(51) Int. Cl.
*A01K 63/06*    (2006.01)
*F24H 1/18*    (2006.01)
(52) U.S. Cl. ........................................ 392/444; 392/441
(58) Field of Classification Search ........... 392/441–464
See application file for complete search history.

(56) References Cited

U.S. PATENT DOCUMENTS

| 4,903,506 | A | * | 2/1990 | Delisle et al. | 62/347 |
| 4,920,763 | A | * | 5/1990 | Provest et al. | 62/378 |
| 5,397,031 | A | * | 3/1995 | Jensen | 222/146.5 |
| 5,797,313 | A | * | 8/1998 | Rothley | 99/483 |
| 6,417,498 | B1 | | 7/2002 | Shields | |
| 6,571,564 | B2 | * | 6/2003 | Upadhye et al. | 62/3.3 |
| 7,651,572 | B2 | * | 1/2010 | Groll et al. | 134/18 |

FOREIGN PATENT DOCUMENTS

| DE | 3332172 | 3/1985 |
| FR | 2580930 | 10/1986 |
| GB | 2185161 | 7/1987 |
| GB | 2228634 | 8/1990 |
| WO | WO 96/25869 | 8/1996 |
| WO | WO 03036193 | 5/2003 |

* cited by examiner

*Primary Examiner* — Daniel L Robinson
(74) *Attorney, Agent, or Firm* — Sherry Womack

(57) ABSTRACT

A babycare heating apparatus comprising a vessel (2;102) for containing water and a heating element (15;115) for heating water held in the vessel, characterized by: a temperature sensor (22;42,123) for sensing a temperature rise effected by operation of the heating element (15); and control means (25;125) for controlling the energizing of the heating element (15;115) in dependence on the output of the temperature sensor (22;42,123) and being configured to de-energize the heating element (15;115) if the change in the temperature, sensed by the sensor (22;42;123), meets a predetermined criterion. The apparatus can be used as a sterilizer or a bottle warmer, and its uses a measure of the rate of heating during operation to determine whether the apparatus has been correctly charged with water.

18 Claims, 19 Drawing Sheets

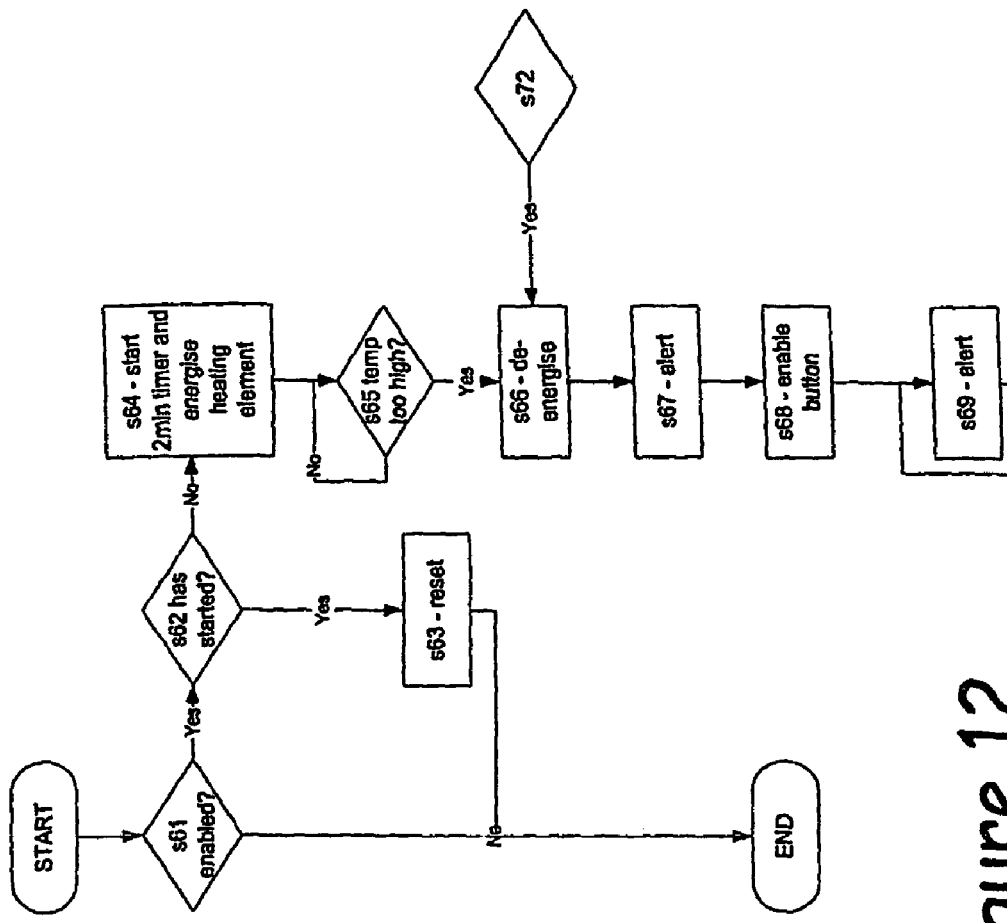

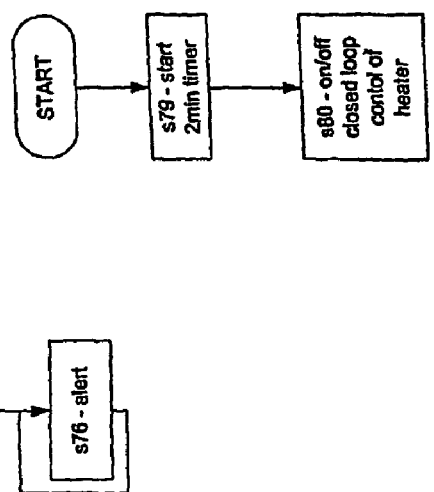
Figure 14
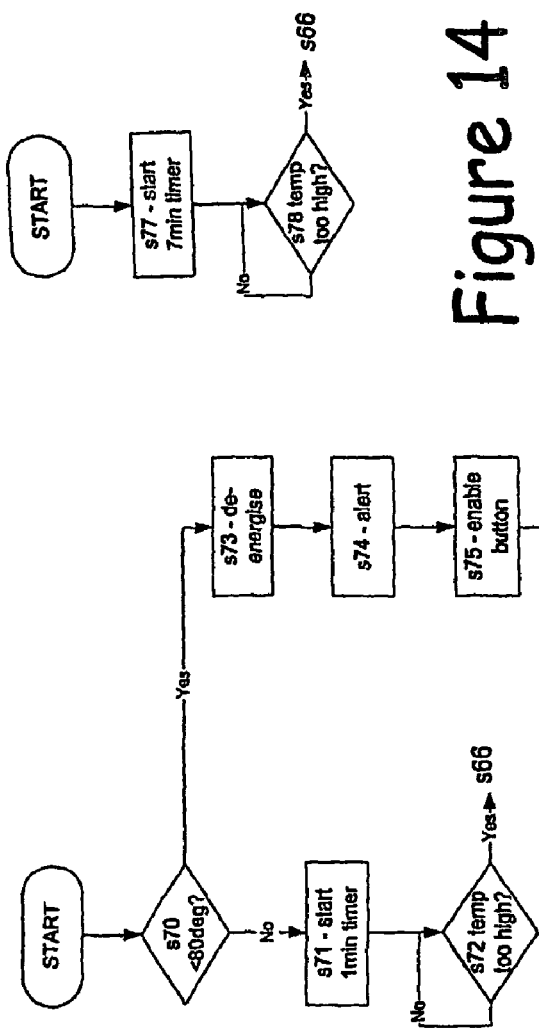
Figure 15
Figure 13

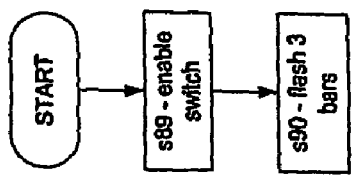
Figure 18
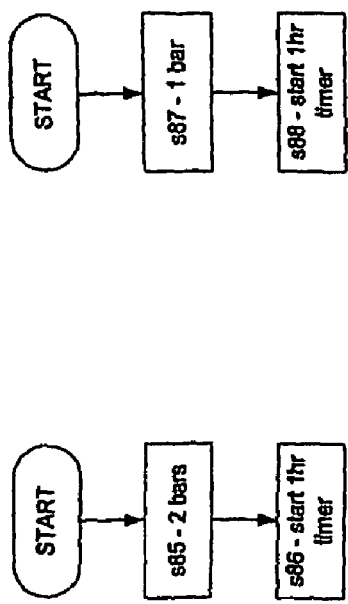
Figure 17
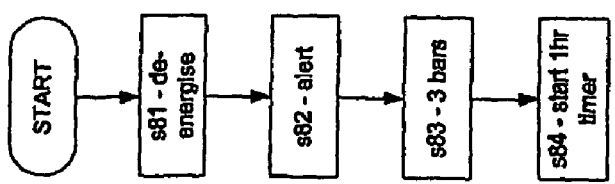
Figure 19
Figure 16

BABYCARE HEATING APPARATUS

FIELD OF THE INVENTION

The present invention relates to babycare heating apparatus.

BACKGROUND TO THE INVENTION

Electric sterilisers for baby feeding bottles are well-known. Such sterilisers are designed to subject the items being sterilised to a temperature of 80° to 100° for several minutes.

In a known design, the operating period is set by loading the apparatus with a predetermined amount of water which evaporates during operation of a heating element. The temperature of the heating element is monitored using a bimetallic thermal switch and when the temperature of the heating element reaches a threshold temperature, indicating that all the water has evaporated or boiled off, the thermal switch opens to cut off the supply of power to the heating element.

A problem with this design of steriliser is that effective sterilisation is dependent on the user charging it with the correct amount of water. Additionally, the effective operational time varies according to the mains voltage and the actual values and ratings of readily available components, which can have quite wide tolerances.

Another heating apparatus familiar to parents is the electric feeding bottle warmer. These devices typically consist of electrically heated bains-marie.

SUMMARY OF THE INVENTION

According to the present invention, there is provided a babycare heating apparatus comprising:
  a vessel for containing water;
  a heating element for heating water held in the vessel;
  a temperature sensor for sensing a temperature rise effected by operation of the heating element; and
  control means for controlling the energising of the heating element in dependence on the output of the temperature sensor,
  wherein the control means is configured to de-energise the heating element if the change in the temperature, sensed by the sensor, meets a predetermined criterion.

The control means may be configured to compare the sensed temperature, at a predetermined time after energising the heating element, with a reference value and said criterion may then comprise said sensed temperature being below said reference value, or to determine a rate of change in the temperature, sensed by the sensor, and compare said rate with a reference value and said criterion may then comprise said rate being greater than a threshold value or to determine a rate of change in the temperature, sensed by the sensor, and compare said rate with a reference value and said criterion may then comprise said rate being less than a threshold value.

Preferably, the control means is configured to determine a rate of change in the temperature, sensed by the sensor, and compare said rate with a reference value and said criterion comprises said rate being within a predetermined range.

Preferably, a metallic heat conductor is provided for conducting heat from the heating element to water in the vessel. More preferably, the temperature sensor is arranged to sense the temperature of said conductor directly.

Alternatively, the vessel may have a wall formed from material that is a poor heat conductor for providing thermal protection for users and the temperature sensor may then be mounted to a reduced thickness portion of said wall. Preferably, the reduced thickness portion has a thickness in the range 0.2 to 1.0 mm.

The present invention may be particularly embodied in a babycare product steriliser or a babycare bottle warmer.

According to the present invention, there is also provided a babycare bottle warmer comprising:
  a vessel for containing water and receiving a feeding bottle to be warmed;
  a chamber,
  a conduit between the vessel and the dumber;
  a valve for opening and closing the conduit;
  a heating element for heating water held in the vessel;
  control means for opening the valve at the end of a bottle heating operation so that hot water in the vessel is conducted to the chamber.

BRIEF DESCRIPTION OF DRAWINGS

Embodiments of the present invention will now be described, by way of example, with reference to the accompanying drawings, in which:

FIGS. 11 to 19 are flowcharts illustrating the sterilising operation of the steriliser of FIG. 9 to sterilise baby feeding bottles;

DETAILED DESCRIPTION OF EMBODIMENTS

Figure 1:
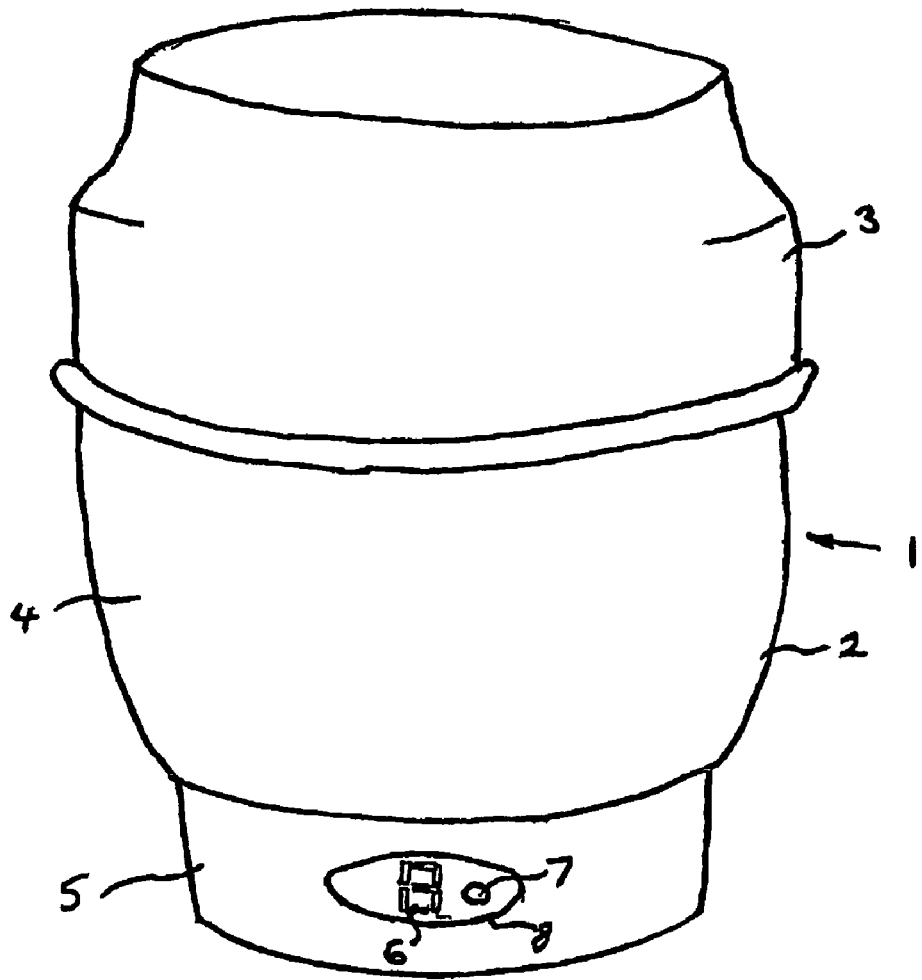
FIG. 1 is a perspective view of a steriliser according to the present invention.

Referring to FIG. 1, a steriliser 1 comprises an opaque body 2 formed from polypropylene and a transparent plastic lid 3, also formed from polypropylene. The body 2 comprises an upper bowl part 4 over a pedestal part 5. Items to be sterilised are placed in the upper bowl part 4. The pedestal part 5 contains the steriliser's electrical components. A 7-segment light emitting diode (LED) display 6 and a push button switch 7 are located in an elliptical aperture 8 in the side wall of the pedestal part 5.

Figure 2:
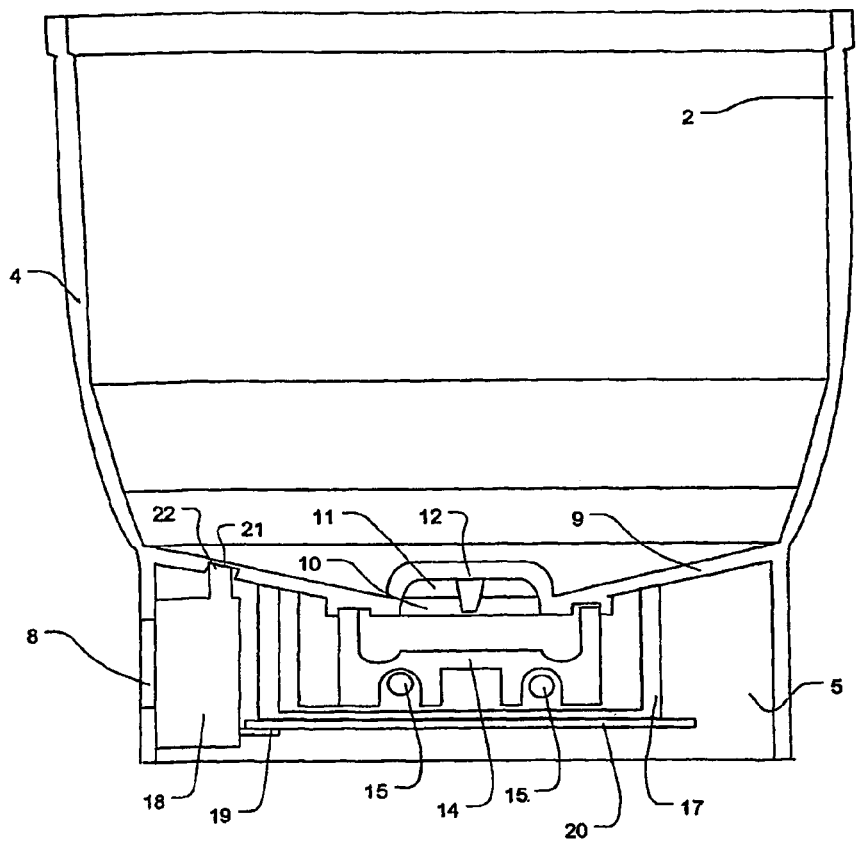
FIG. 2 is a schematic sectional view of the steriliser of FIG. 1.

Referring to FIG. 2, which omits some structural details unnecessary for an understanding of the present invention, the floor 9 of the bowl part 4 is slightly dished and has a central roofed aperture 10. Gaps 11 between the roof 12, over the aperture 10, and the surrounding part of the floor 9 open into a small cast metal trough 14. A electric heating element 15, rated at 500 W at 110V, is mounted to the underside of the trough 14. The trough 14 and its heating element 15 are clamped in place by a cover 17 that is screwed to pillars (not shown) projecting from the underside of the floor 9. A watertight seal is formed between the trough 14 and the floor 9, preferably using an elastomeric sealing member.

An electronic assembly 18 is mounted in the pedestal behind the elliptical aperture 8. The electronic assembly 18 includes a triac 19, the purpose of which is described below. The triac 19 is thermally coupled to a planar heatsink 20 that extends below the cover 17.

A small area of the floor 9, located above the electrical assembly, is much thinner, about 0.5 mm thick, than the rest of the floor 9 forming a recess 21. A thermistor 22 is mounted in the recess 21. The thermistor 22 location is not covered by water when the correct amount of water has been added to the steriliser 1.

Figure 3:
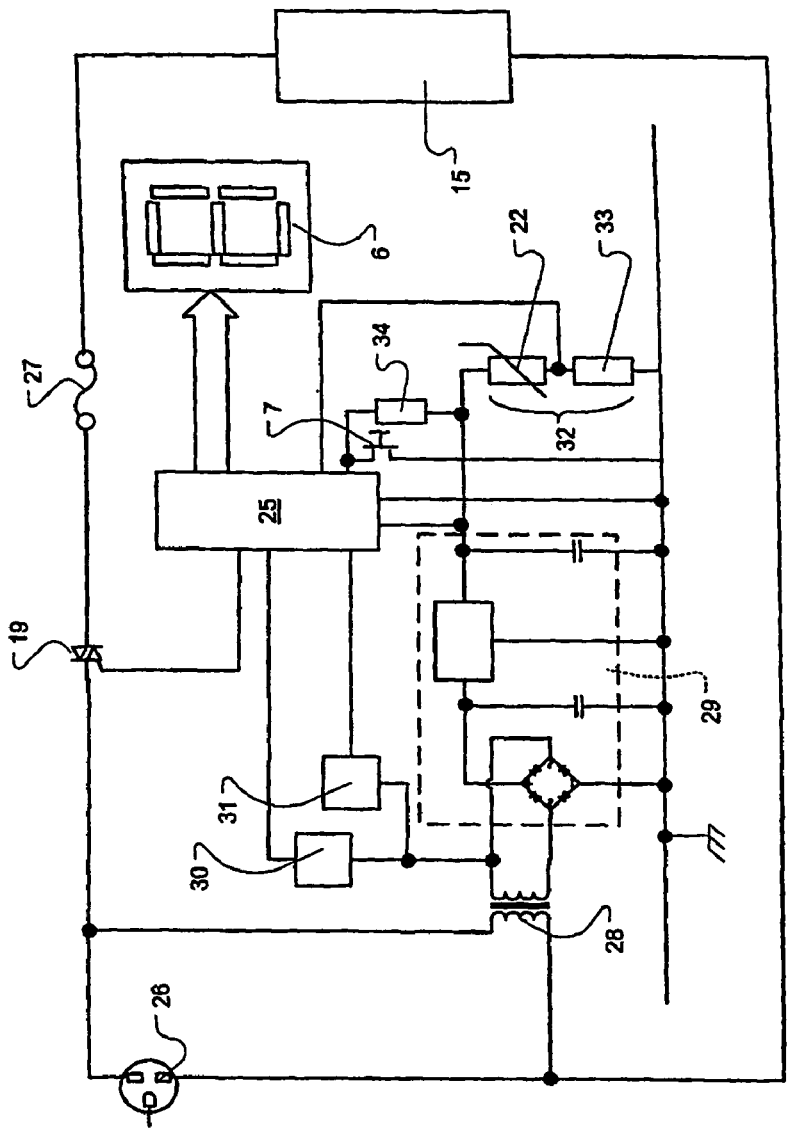
FIG. 3 is a block diagram of the control electronics of the steriliser of FIG. 1.

Referring to FIG. 3, the electronic assembly 18 includes an electronic control circuit based around a microcontroller 25. The steriliser 1 is powered from the mains and has a plug 26 for plugging into a mains outlet socket. The triac 19, a thermal fuse 27 for protecting the steriliser 1 against overheating, and the heating element 15 are connected in series between the live and neutral pins of the plug 26.

A transformer 28 and a rectifying and regulating circuit 29 provide a dc supply for powering the microcontroller 25 from the input mains. The inputs of a zero crossing detector 30 and a peak voltage detecting circuit 31 are connected to the secondary of the transformer 28.

A potential divider 32, comprising the thermistor 22 and a resistor 33, is connected between the +V output of the rectifying and regulating circuit 29 and earth. The output of the potential divider 32, i.e. the junction between the thermistor 22 and the resistor 29, is connected to an analogue-to-digital converter input of the microcontroller 25.

The 7-segment LED display 6 is driven from a port of the microcontroller 25. Another port of the microcontroller 25 controls the triac 19. Finally, the pushbutton switch 7 is connected to an interrupt port of the microcontroller 25. A pull-up resistor 34 is connected to this interrupt port which is connected to 0V when the switch 7 is closed.

The operation of the steriliser 1 will now be described.

Figure 4:
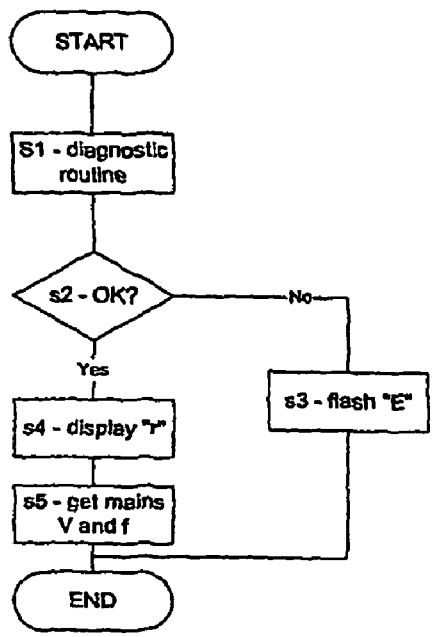
FIGS. 4 to 8 are flowcharts illustrating the sterilising operation of the steriliser of FIG. 1.

Referring to FIG. 4, when the steriliser 1 is energised from the mains, the microcontroller 25 performs an initial diagnostic routine (step s1). If a fault is detected (step s2), the microcontroller 25 causes the LED display 6 to flash E for "error" (step s3). However, if no faults are detected, the microcontroller 25 causes the LED display 6 to display "r" for "ready" (step s104). Then the microcontroller 25 determines the mains voltage and frequency from the outputs of the zero-crossing detector 30 and the peak voltage detecting circuit 31 and saves these values (step s5).

Figure 5:
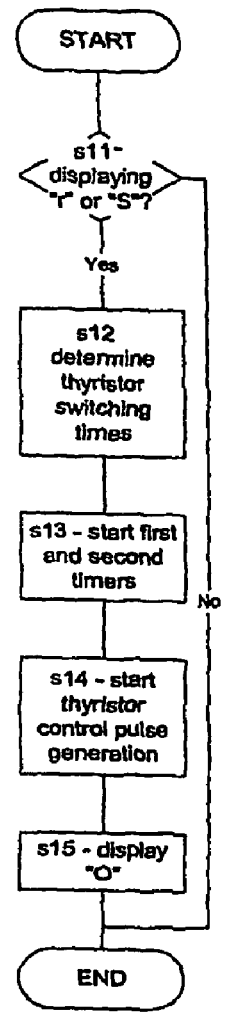

Referring to FIG. 5, when the user operates the switch 7, the microcontroller 25 first checks that "r" or "S" is being displayed (step s11). If neither "r" or "S" is being displayed, the microcontroller 25 reads the stored mains voltage and frequency values and determines switching times for the triac 18 (step s12). For instance, if the mains supply is 110V at 60 Hz, the triac 19 needs to be turned on at the start of each half-cycle which requires a pulse every 16.7 ms. However, if the mains supply is 220V at 50 Hz, the triac needs to be turned on halfway through each half-cycle which requires a pulse 5 ms after each zero-crossing at a rate of one every 20 ms. At substantially the same time, the microprocessor 25 starts first and second timers with respectively 40 seconds and 60 seconds durations (step s13).

The microcontroller 25 then begins to output the necessary triac control pulses (step s14) and causes the LED display 6 to display "O" for operating (step s15).

Figure 6:
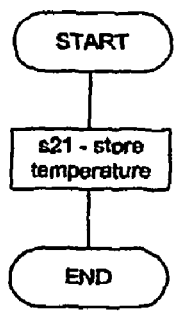

Referring to FIG. 6, when the first timer has timed out, the microcontroller 25 reads and stores the output of the potential divider 32, which represents the temperature in the bowl part 4 of the steriliser 1 (step s21).

Figure 7:
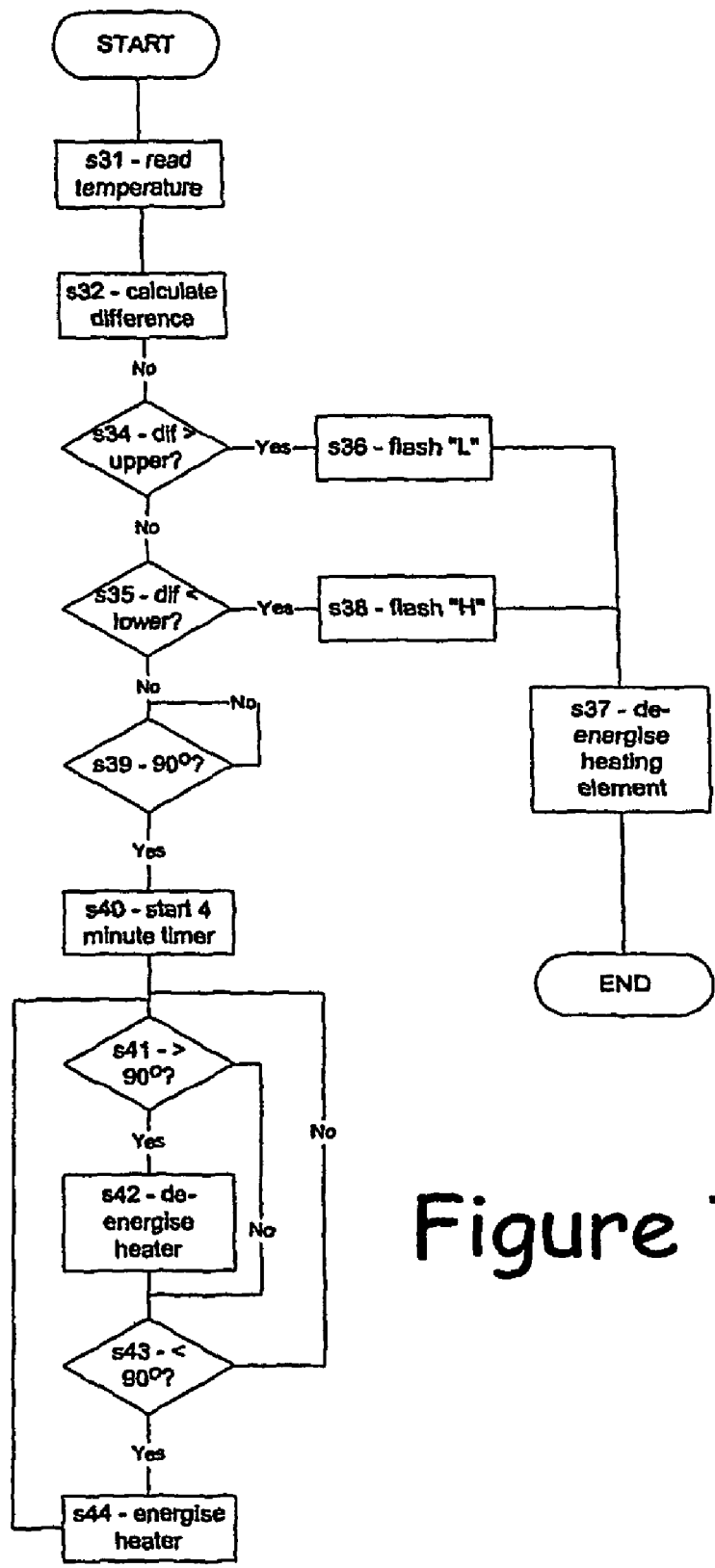

Referring to FIG. 7, when the second timer times out, the microcontroller 25 reads the output of the potential divider (step s31). The first value is then subtracted from the new, second value (step s32) and the result compared with upper and lower thresholds (steps 33 and 34). The upper and lower thresholds correspond to the rate of heating to be expected with the minimum and maximum acceptable amounts of water in the steriliser 1 under normal domestic operating conditions.

If the difference between the first and second values is above the upper threshold, the user has placed insufficient water in the steriliser 1. The microcontroller 25 responds to this by causing the LED display to flash "L" for "water level too low" (step s36) and ceasing to send pulses to the triac 18 to de-energise the electric heating element 15 (step s37). If the difference between the first and second values is below the lower threshold, the user has placed too much water in the steriliser 1. The microcontroller 25 responds to this by causing the LED display 6 to flash "H" for "water level too high" (step s38) and ceasing to send pulses to the triac 18 to de-energise the electric heating element 15 (step s37).

If the difference between the first and second values is within the range bounded by the upper and lower thresholds, the microcontroller 25 continues to supply pulses to the triac 18 while monitoring the output of the potential divider 32.

When the monitored voltage reaches a level, corresponding to a temperature of 90° in the upper bowl pan 4 of the steriliser 1 (step s39), a four-minute timer is started in the microcontroller 25 (step s40).

The microprocessor 25 then enters a loop (steps s41 to s44) to perform simple on off control of the temperature in the steriliser 1. The temperature is controlled by de-energising the heating element 15 when the temperature rises above 90° and energising the heating element when the temperature falls below 90°.

Figure 8:
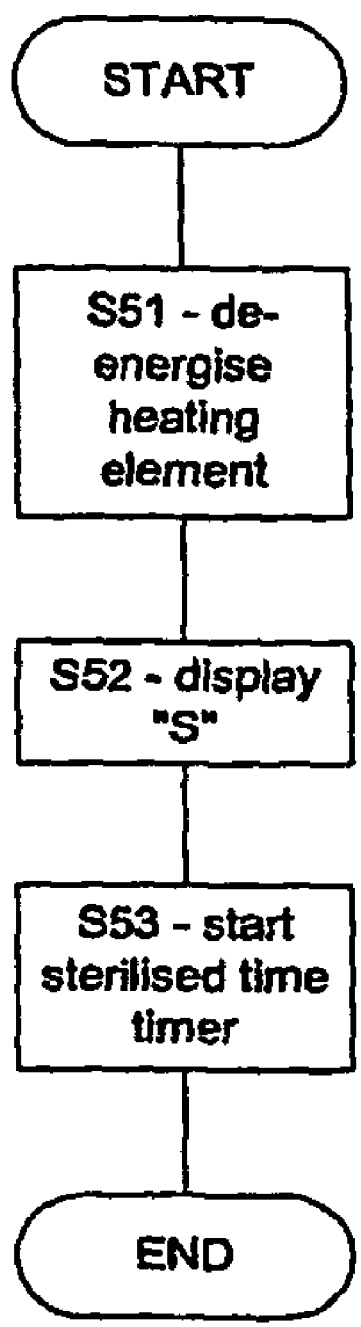

Referring to FIG. 8, when the four-minute timer times out, the microcontroller 25 ceases to send pulses to the triac 19 to de-energise the heating element 15 (step s51) and causes the LED display to display "S" for sterilised (step s52). At substantially the same time, a sterilised time timer is started in the microcontroller 25 (step s53) and the "S" continues to be displayed until the sterilised time timer expires after 3 hours, when it is replaced by "r".

Figure 9:
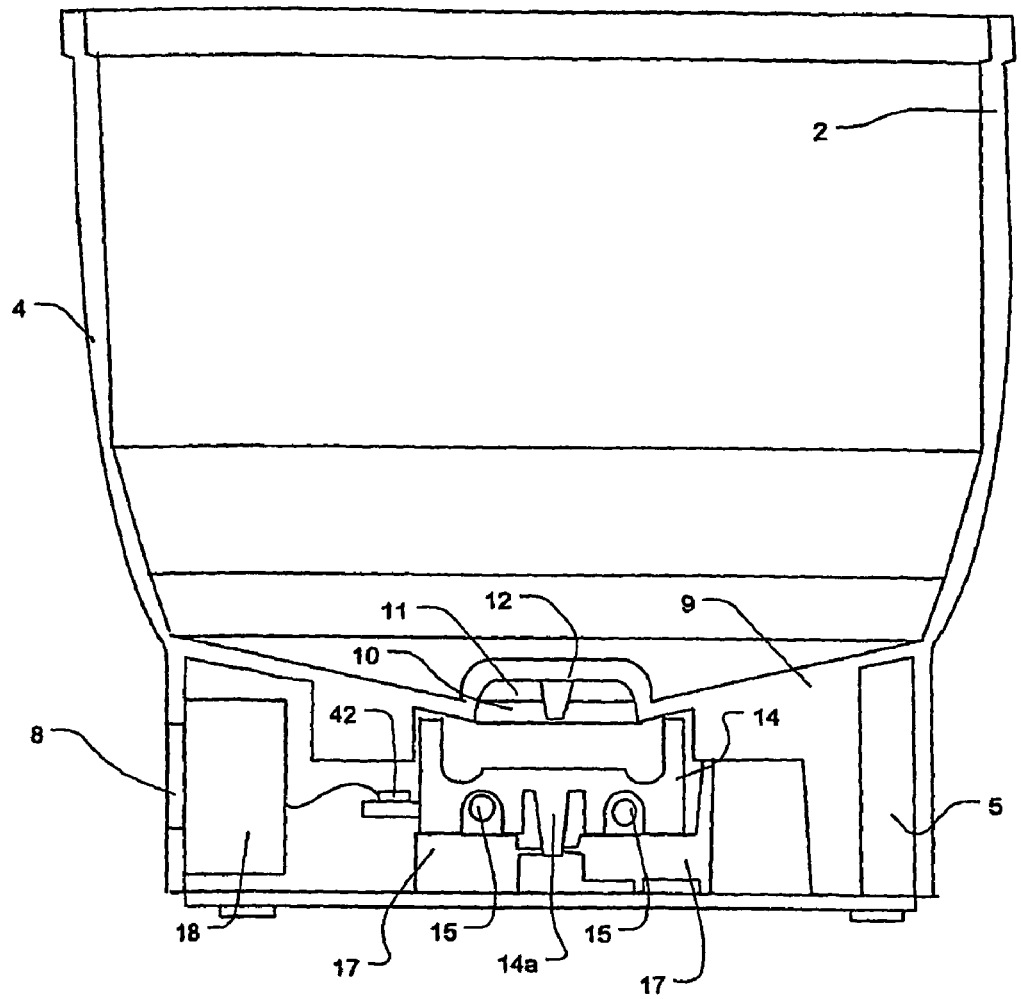
FIG. 9 is a schematic sectional view of a simplified steriliser.

Referring to FIG. 9, in a simplified steriliser, a thermistor 42 is mounted to the cast trough 14 instead of in the floor 9 as in the preceding embodiment. The heatsink 20 is also absent, a floor 5a has been added to the pedestal part 5 and the cover 17 modified to extend from the floor 5a of the pedestal part 5 to the cast trough 14. A central locating finger 14a projects downwards from the cast trough 14 and is received in a hole in the cover 17.

Figure 10:
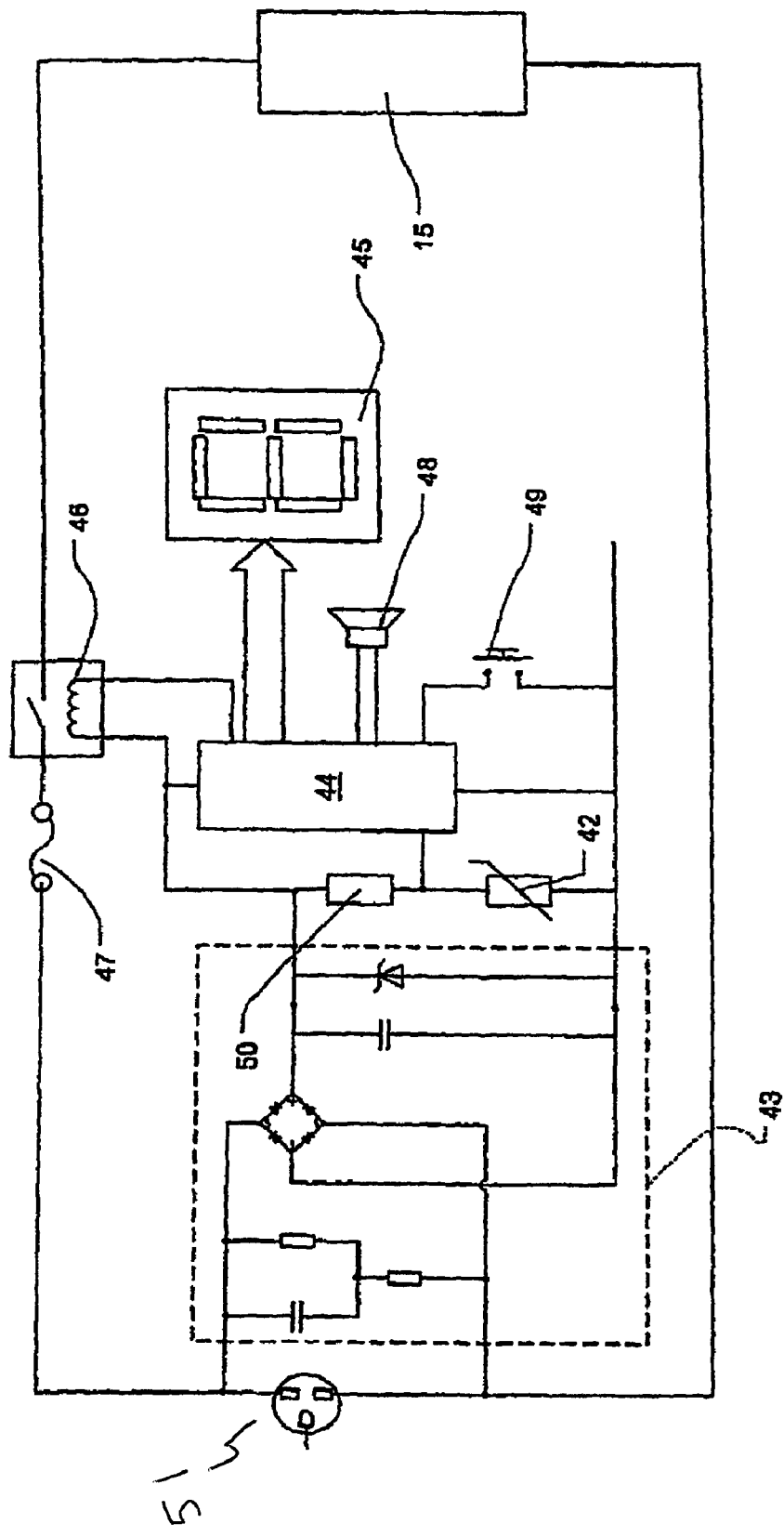
FIG. 10 shows the control electronics of the steriliser of FIG. 9.

Referring to FIG. 10, the circuit of the simplified steriliser comprises a transformerless dc power supply 43, a microcontroller 44, a 7-segment LED display 45, a relay 46, a fuse 47, a piezo sounder 48, a pushbutton switch 49 and a potential divider consisting of the thermistor 42 and a resistor 50. The microcontroller 44 is powered from the dc power supply 43 which rectifies and reduces the mains voltage received via a mains plug 51. The potential divider has the resistor 50 connected to the +V output of the dc power supply 43 and the thermistor 42 connected to the earth/−V output of the dc power supply 43. The node between the thermistor 42 and the resistor 50 is connected to an analogue-to-digital converter input of the microcontroller 44. The piezo sounder 48 is driven directly from outputs of the microcontroller 44. The segments of the LED display 45 and the coil of the relay 46 are also energised directly by the microcontroller 44. The pushbutton switch 49 is connected between an interrupt port of the microcontroller 44 and earth.

The fuse 47 and the switch of the relay 46 are connected in series between the to mains live input and one end of the heating element 15. The other end of the heating element 15 is connected to the mains neutral input.

The operation of the simplified steriliser will now be described.

Referring to FIG. 11, when the simplified steriliser is powered up, the microcontroller 44 causes to LED display 45 to display "0" (step s60).

Referring to FIG. 12, closing the pushbutton switch 49 generates an interrupt. If responding to the switch closing is not enabled (step s61) nothing happens. However, if responding to the switch 49 closing is enabled, which is the case when the steriliser has been energised and the switch 49 has not yet been closed, the switch closing is responded to. If a sterilising operation is in progress (step s62), the steriliser is reset to its initial powered but not operating state (step s63). However, if a sterilising operation is not in progress, a 2-minute timer is started and the relay 46 is closed to energise the heating element 15 (step s64).

Once the heating element 15 has been energised, the temperature of the cast trough 14 is monitored using the output of the potential divider (step s65) and, if the temperature exceeds 110° C., it is determined that the steriliser has boiled dry and the relay 46 is opened to de-energise the heating element 15 (step s66) and an alert is signalled by operating the piezo sounder 48 and flashing "d" on the LED display 45 five times (step s67). Responding to the switch 49 being closed is then enabled (step s67) and the signalling of the alarm continued (step s68). If the switch 49 is now closed, step s63 will be performed and the steriliser reset.

Referring to FIG. 13, when the 2 minute timer times out, the temperature of the cast trough 14 is tested (step s70) and, if it is over 80° C., a 1-minute timer is started (step s71) and then monitoring of the temperature of the cast trough 14 is performed (step 972). If the temperature is determined to exceed 110° C. at step s72, the flow moves to step s66 of FIG. 12.

However, if the temperature of the cast trough 14 is found not to be above 80° C. at step s70, it is determined that the steriliser has been overfilled and the relay 46 is opened to de-energise the heating element 15 (step s73) and an alert is signalled by operating the piezo sounder 48 and flashing "F" on the LED display 45 five times (step s74). Responding to the switch 49 being closed is then enabled (step s75) and the signalling of the alarm continued (step s76). If the switch 49 is now closed, step s63 will be performed and the steriliser reset.

Referring to FIG. 14, when the 1-minute timer times out, a 7-minute timer is started and '9' is displayed by the LED display 45 (step s77). The temperature of the cast trough 14 is then monitored (step s78) and, if it exceeds 110° C., flow moves to step s66 in FIG. 12.

Referring to FIG. 15, when the 7-minute timer times out, the microcontroller 44 starts a second 2-minute timer (step s79) and performs simple on/off closed loop control of the heating element 15 to maintain the temperature of the cast trough 14 at about 110° C. (step s80).

Referring to FIG. 16, when the second 2-minute time times out, the heating element 15 is de-energised (step s81) and an alert signalled to indicate the completion of the sterilising process (step s82). The alert signalling comprises energising the piezo sounder 48 five times while flashing "O" on the LED display 45. When the alert is complete, "=" is displayed by the led display 45 (step s83) and a first 1-hour timer is started (step s84).

Referring to FIG. 17, when the first 1-hour timer times out, the displayed symbol on the LED display 45 is changed to "=" (step s85) and a second 1-hour timer is started (step s86).

Referring to FIG. 18, when the second 1-hour timer times out, the displayed symbol on the LED display 45 is changed to "=" (step s87) and a third 1-hour timer is started (step s88).

Referring to FIG. 19, when the third 1-hour timer times out, the microcontroller 44 causes "=" to be flashed by the LED display 45 (step s89) and responding to closing of the switch 49 is enabled (step s90) to allow the steriliser to be reset.

Bottle warmers according to the present invention will now be described.

Figure 20:
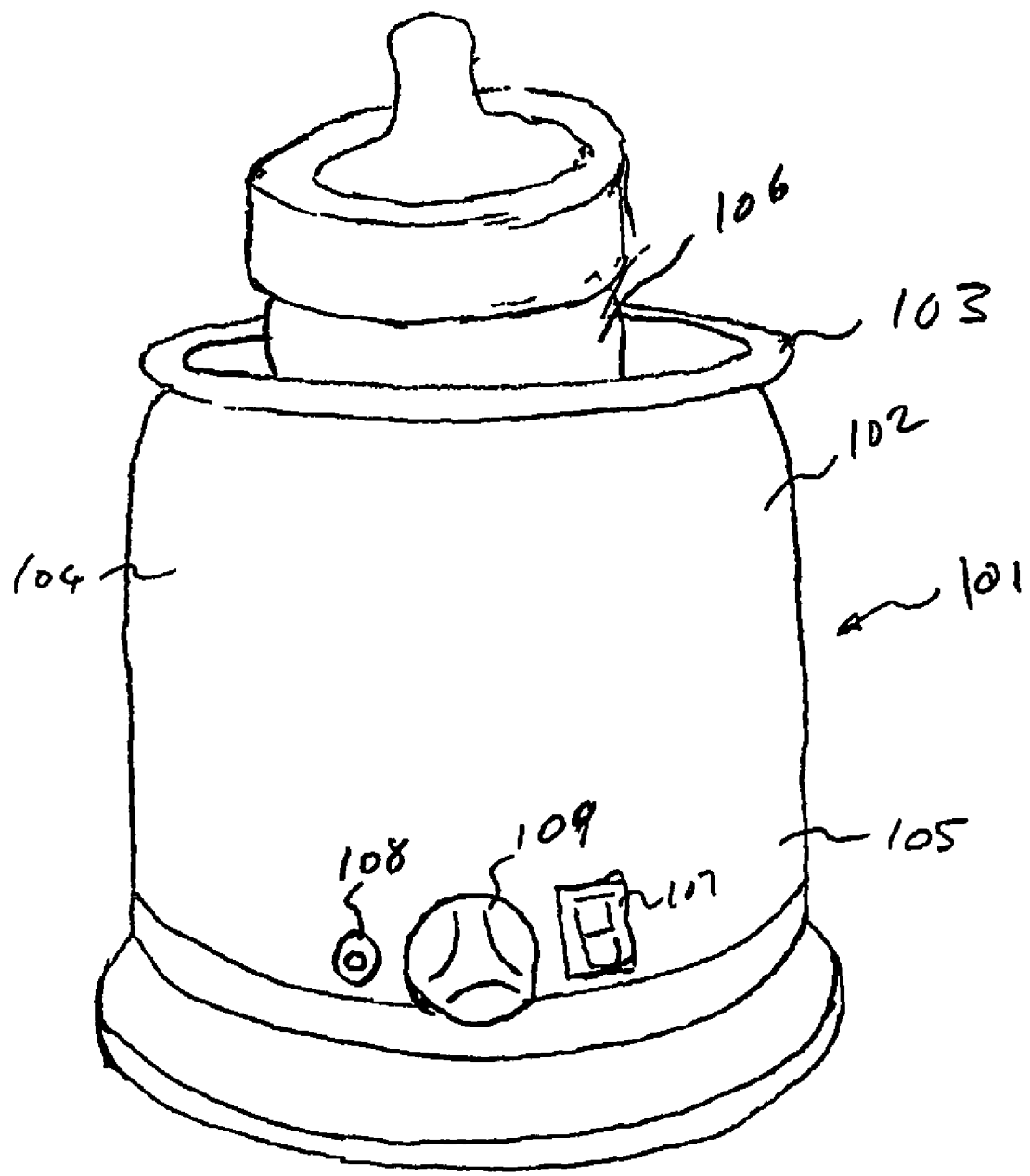
FIG. 20 is a perspective view of a feeding bottle warmer according to the present invention.

Referring to FIG. 20, a bottle warmer 101 comprises a body 102 formed from an opaque plastics material e.g. polypropylene. The body 102 comprises an upper bowl part 104 over a base part 105. A basket 103 is removably received in the bowl part 104 and provides a secure resting place for feeding bottles 106 during warming.

The pedestal part 105 contains the warmer's electrical components. A 7-segment LED display 107, a push button switch 108 and a power control knob 109 are provided on the side of the base part 105.

Figure 21:
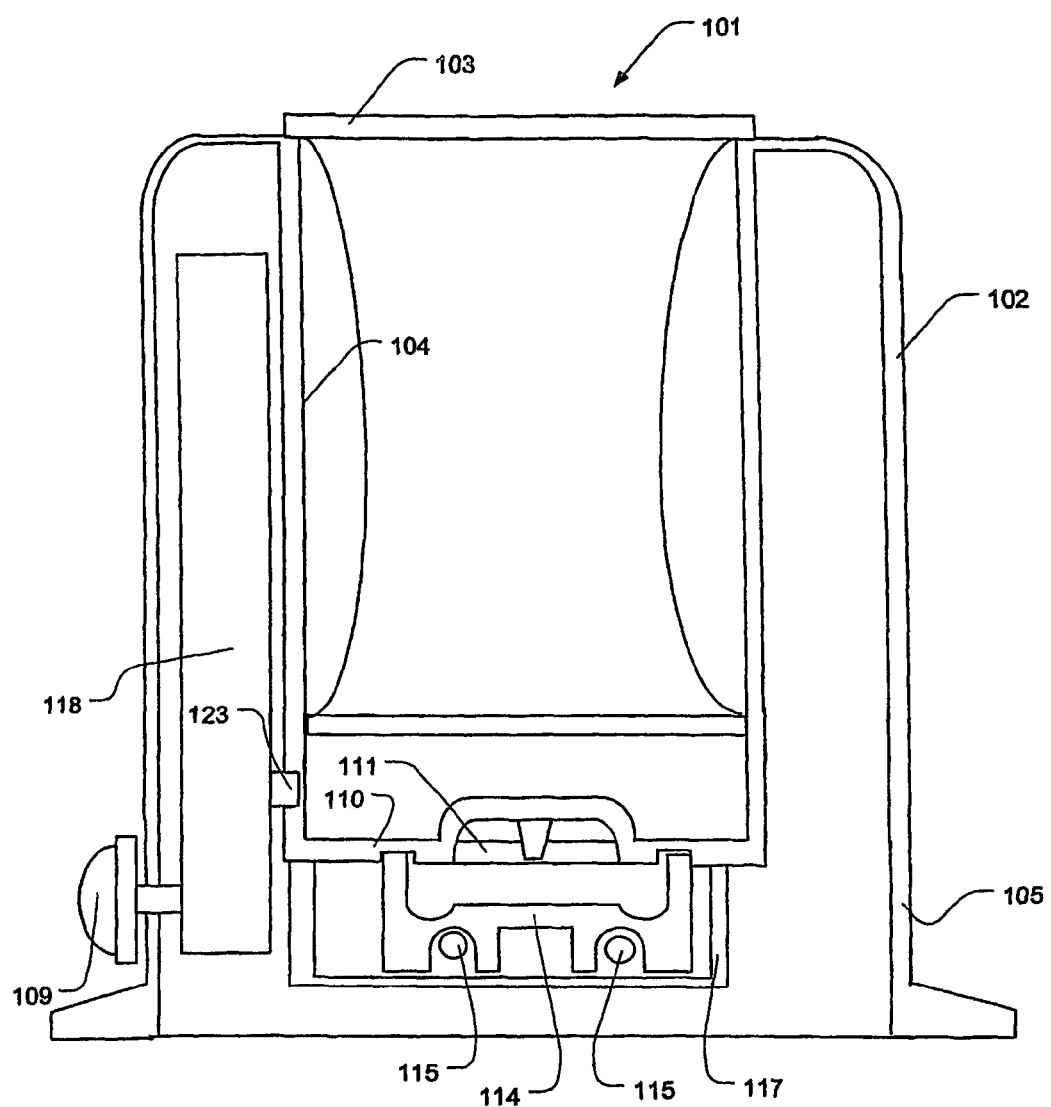
FIG. 21 is a schematic sectional view of the bottle warmer of FIG. 6.

Referring to FIG. 21, which omits some structural details unnecessary for an understanding of the present invention, the floor 110 of the bowl part 104 has a roofed central aperture 111 which opens into a small cast metal trough 114. A electric heating element 115, rated at 200 W at 110V, is mounted to the underside of the trough 114. The trough 114 and its heating element 115 are clamped in place by a cover 117 that is screwed to pillars (not shown) projecting from the underside of the floor 110. The side of the bowl part 104 is hollow.

An electronic assembly 118 is mounted in the hollow side of the bowl part 104 and extends into the base part 105. The electronic assembly includes the switch 107, a three-position rotary switch 119 (see FIG. 11), operated by means of the knob 109, and the LED display 107. The electronic assembly 118 includes a triac 120 (FIG. 22), the purpose of which is described below. The triac 120 is thermally coupled to a heatsink (not shown).

A small area of the inner wall of the side of the bowl portion 104 is much thinner, about 0.5 mm thick, than the rest of the inner wall. A recess 122 is formed where the wall 110 is thinned and a thermistor 123 is mounted in the recess 122.

For use, water is placed between the bowl part 104 so that the basket 103 is partial submerged. The water is heated by the heating element 15 and heat is transferred from the water to the bottle 106 in the basket 103.

Figure 22:
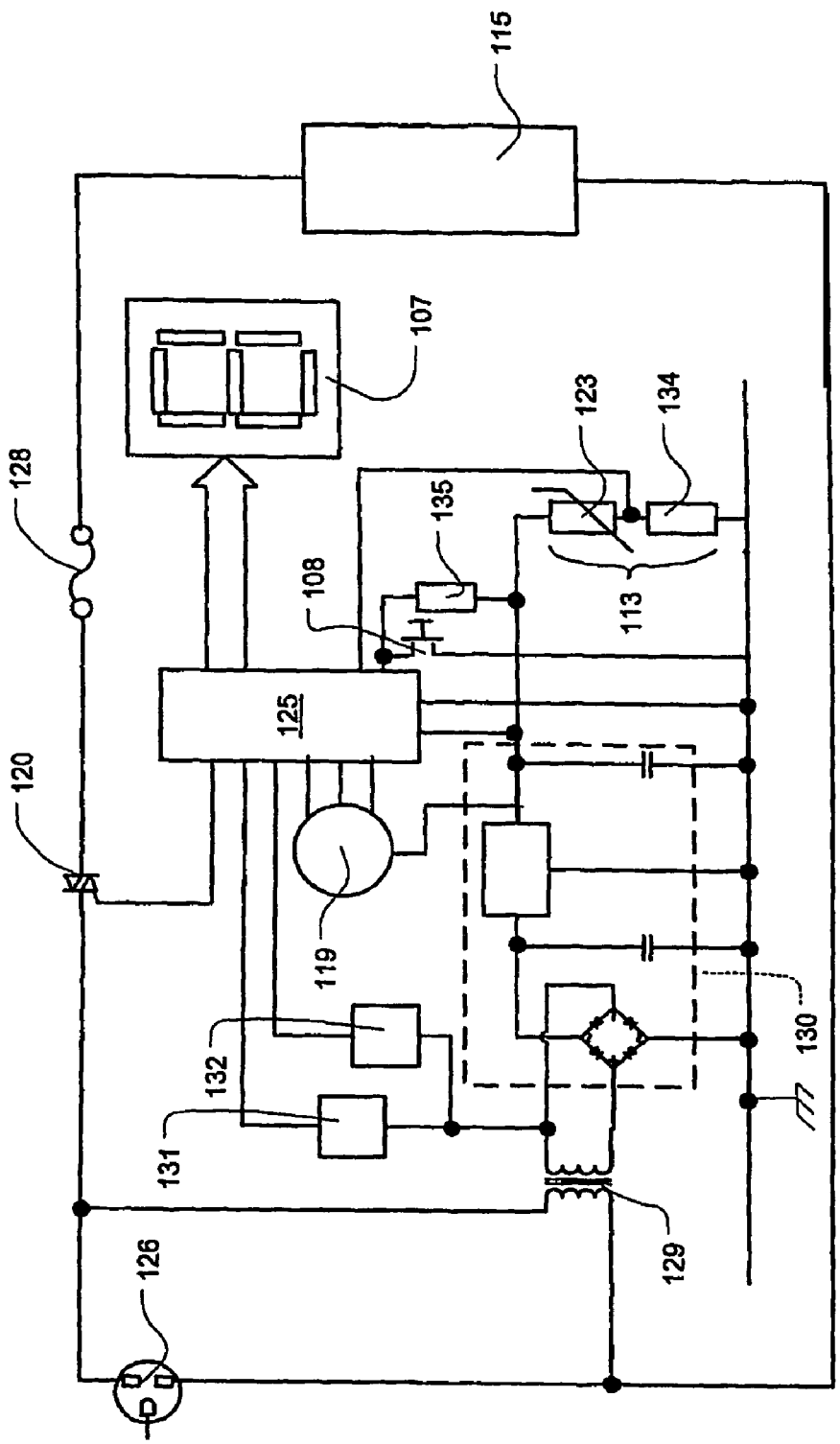
FIG. 22 is a block diagram of the control electronics of the bottle warmer of FIG. 6.

Referring to FIG. 22, the electronic assembly 118 includes an electronic control circuit based around a microcontroller 125. The warmer 101 is powered from the mains and has a plug 126 for plugging into a mains outlet socket. The triac 120, a thermal fuse 128 for protecting the warmer 101 against overheating, and the heating element 115 are connected in series between the live and neutral pins of the plug 126.

A transformer 129 and a rectifying and regulating circuit 130 provide a dc supply for powering the microprocessor 125 from the input mains. The inputs of a zero crossing detector 131 and a peak voltage detecting circuit 132 are connected to the secondary of the transformer 129.

The rotary switch 119 has its terminal connected to the +V output of the rectifying and regulating circuit 130 and its other terminals connected to respective input pins of an input port of the microcontroller 125. Pull-down resistors (not shown) are connected between these pins and 0V. Thus, the three positions of the switch 119 provide three different 3-bit values to the microcontroller 125.

A potential divider 133, comprising the thermistor 123 and a resistor 134, is connected between the +V output of the rectifying and regulating circuit 130 and earth. The output of the potential divider 133, i.e. the junction between the thermistor 123 and the resistor 134, is connected to a analogue-to-digital converter input of the microcontroller 125.

The 7-segment LED display 107 is driven from a port of the microcontroller 125. Another port of the microcontroller 125 controls the triac 120. Finally, the pushbutton switch 108 is connected to an interrupt port of the microcontroller 125. A pull-up resistor 135 is connected to this interrupt port which is connected to 0V when the switch 108 is closed.

The operation of the bottle warmer 101 will now be described.

Figure 23:
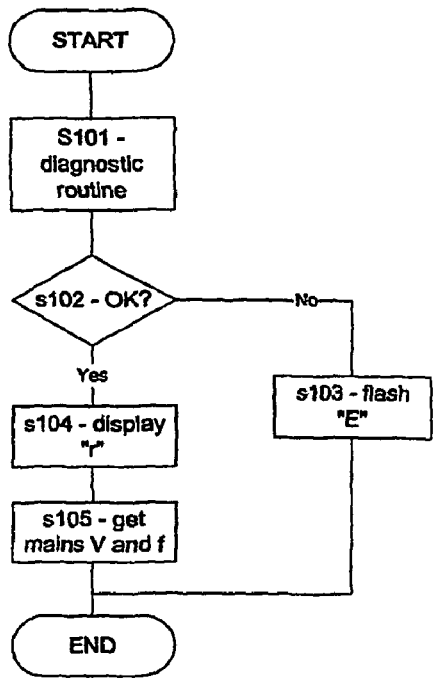
FIGS. 23 to 27 are flowcharts illustrating the warming operation of the bottle warmer of FIG. 20.

Referring to FIG. 23, when the steriliser 1 is energised from the mains, the microcontroller 125 performs an initial diagnostic routine (step s101). If a fault is detected (step s102), the microcontroller 125 causes the LED display 107 to flash E for "error" (step s103). However, if no faults are detected, the microcontroller 125 causes the LED display 6 to display "r" for "ready" (step s104). Then the microcontroller 25 determines the mains voltage and frequency from the outputs of the zero-crossing detector 30 and the peak voltage detecting circuit 31 and saves these values (step s5).

Figure 24:
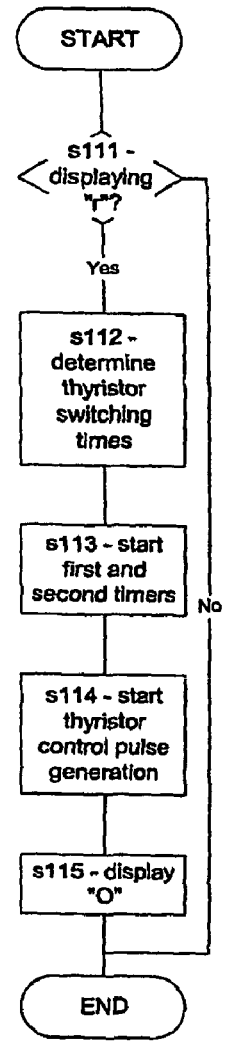

Referring to FIG. 24, when the user operates the switch 108 with a single push, the microcontroller 125 first checks that "r" is being displayed (step s111). If "r" is not being displayed, the microcontroller 125 reads the stored mains voltage and frequency values and determines switching times for the triac 120 on the basis of these and the power level indicated by the position of the three-way switch 199 (step s112). At substantially the same time, the microprocessor 25 starts first and second timers with respectively 40 s and 60 s durations (step s113).

The microcontroller 25 then begins to output the necessary triac control pulses (step s114) and causes the LED display 107 to display "O" for operating (step s115).

Figure 25:
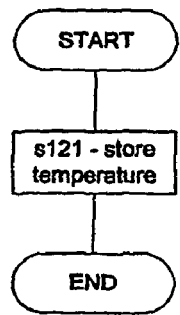

Refuting to FIG. 25, when the first timer has timed out, the microcontroller 25 reads and stores the output of the potential divider 133, which represents the temperature in the bowl part 104 of the warmer 101 (step s121).

Figure 26:
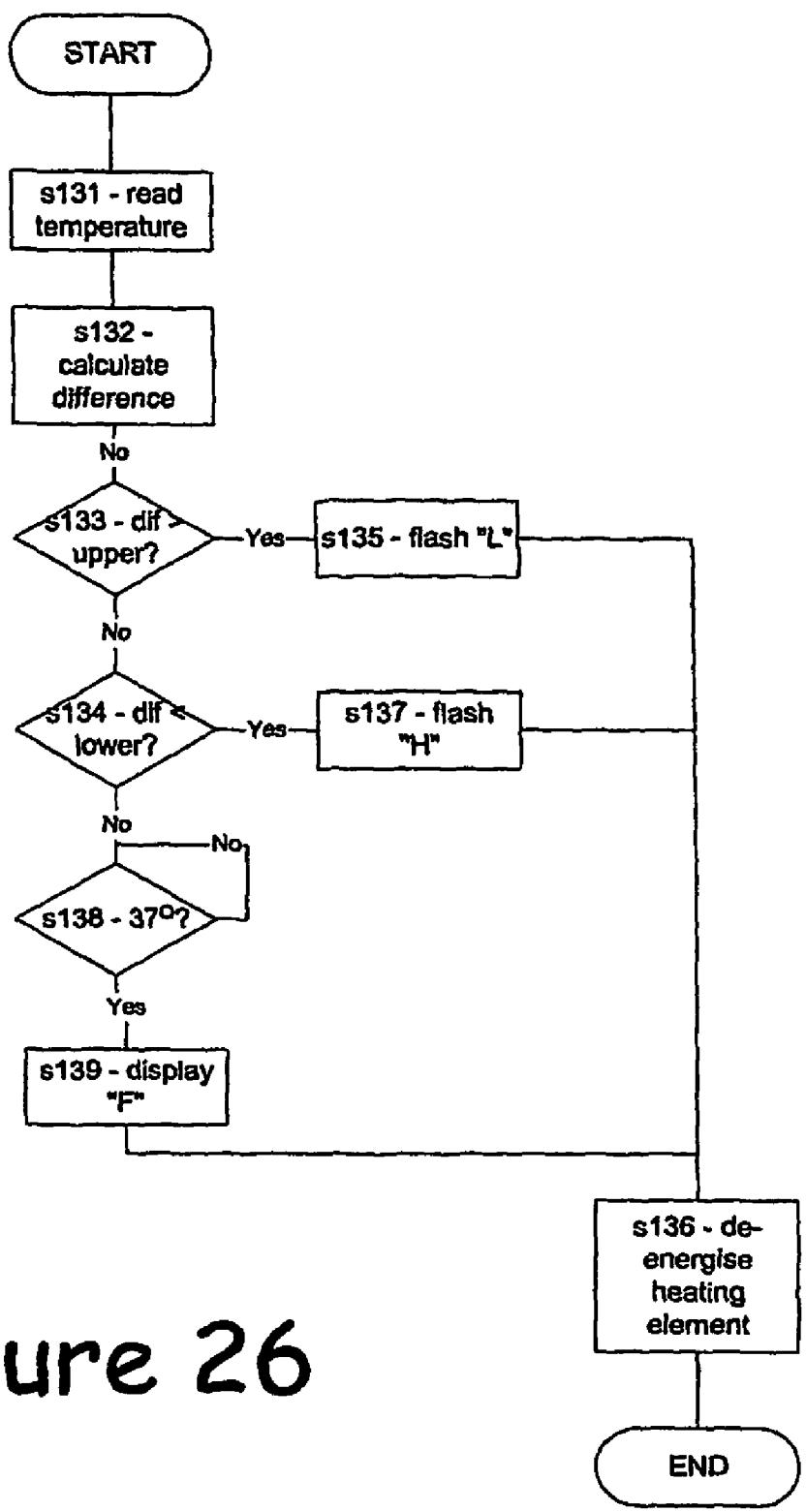

Referring to FIG. 26, when the second timer times out, the microcontroller 25 read the output of the potential divider (step s131). The first value is then subtracted from the new, second value (step s132) and the result compared with upper and lower thresholds (steps 133 and 134). The upper and lower thresholds to correspond to the range of rates of heating consistent with safe and effective heating of milk. If the rate of heating is too high, the target temperature may be overshot and the milk overheated. If the rate of heating is too low, the milk may not reach the required temperature.

If the difference between the first and second values is above the upper threshold, the user has placed insufficient water and/or milk in the warmer 101, or selected too high a power level. The microcontroller 125 responds to this by causing the LED display to flash "L" for contents too low (step s135) and ceasing to send pulses to the triac 120 to de-energise the electric heating element 115 (step s136). If the difference between the first and second values is below the lower threshold, the user has placed too much water and/or milk in the warmer 101 or selected too low a power level. The microcontroller 125 responds to this by causing the LED display 6 to flash "H" for "contents too high" (step s137) and ceasing to send pulses to the triac 120 to de-energise the electric heating element 115 (step s136).

If the difference between the first and second values is in the range bounded by the upper and lower thresholds, the microcontroller 125 continues to supply pulses to the triac 120 while monitoring the output of the potential divider 133.

When the monitored voltage reaches a level, corresponding to a temperature of 37° in the milk being heated (step s138), "F" for finished is displayed by the LED display 107 (step s140).

A second mode of operation is started by a double push on the pushbutton switch 107.

Figure 27:
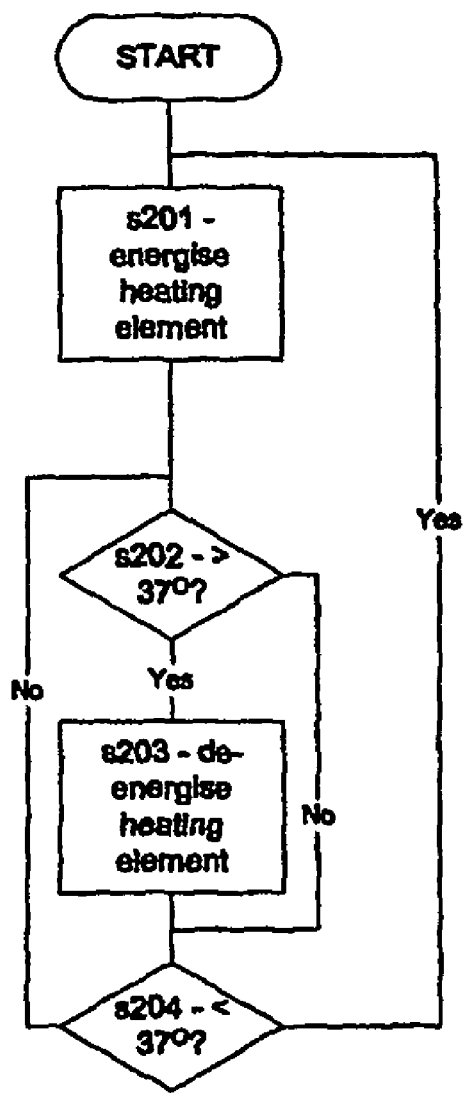

Referring to FIG. 27, the heating element 115 is energised at full power (step s201) until the water in the warmer 101 is at 37° (step s202). The power supply to the heating element 115 is then turned off and on by the microprocessor 125 to keep the water at 37° (steps s201 to s204). Keeping the water at 37° ensures that the milk being warmed will eventually reach 37° without risk of overheating.

Figure 28:
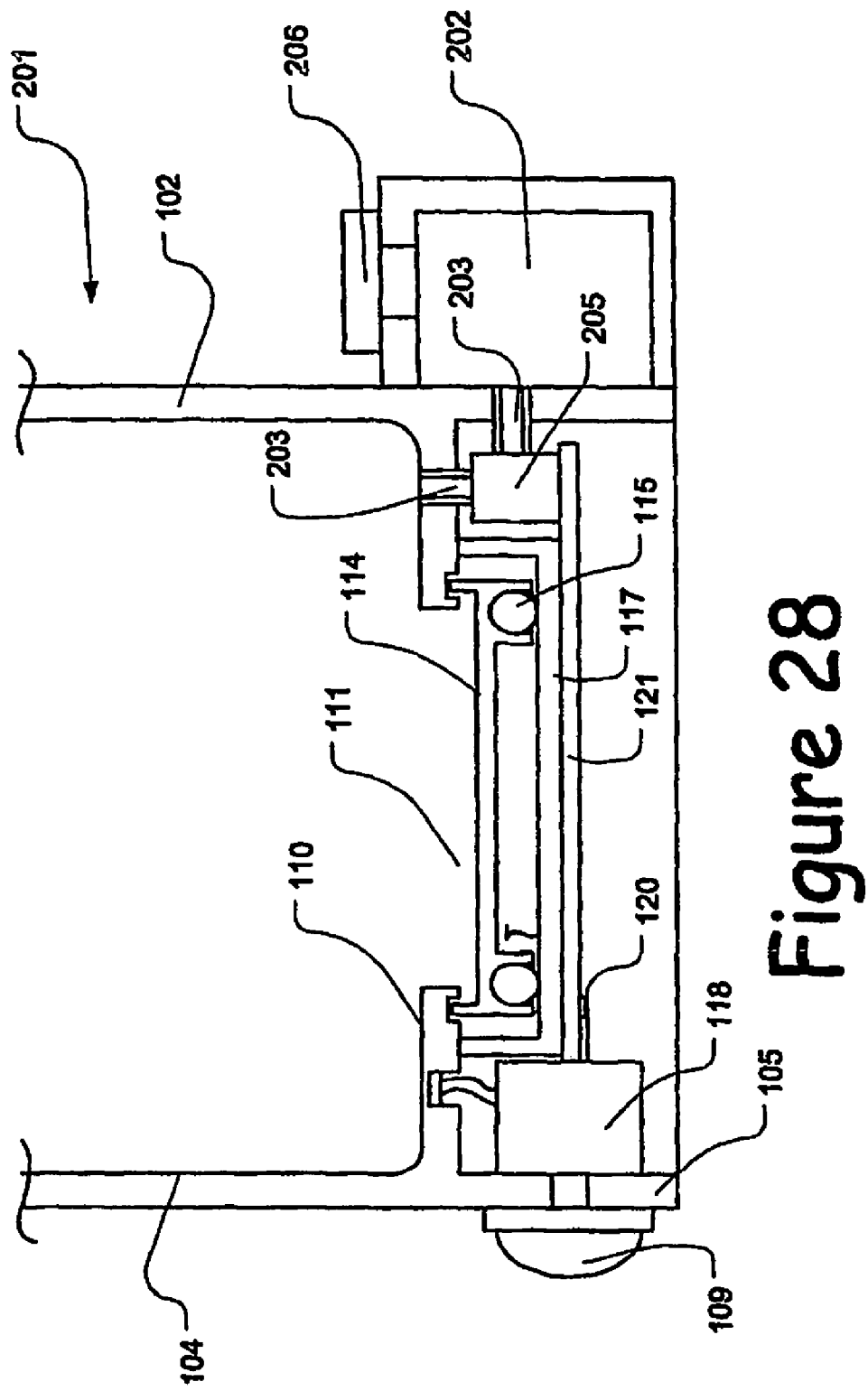
FIG. 28 is a schematic sectional view of another bottle warmer according to the present invention.

Referring to FIG. 28, a second bottle warmer 201 according to the present invention is similar to that shown in FIG. 20. However, it differs in that a chamber 202 is provided within its base 105. A passageway 203 extends from the interior of the bowl part 104 to the chamber 202. A solenoid valve 205 is provided for opening and closing the passageway 203. A plug 206 can be removed from the bottom of the chamber 202 so that its contents can be drained.

Figure 29:
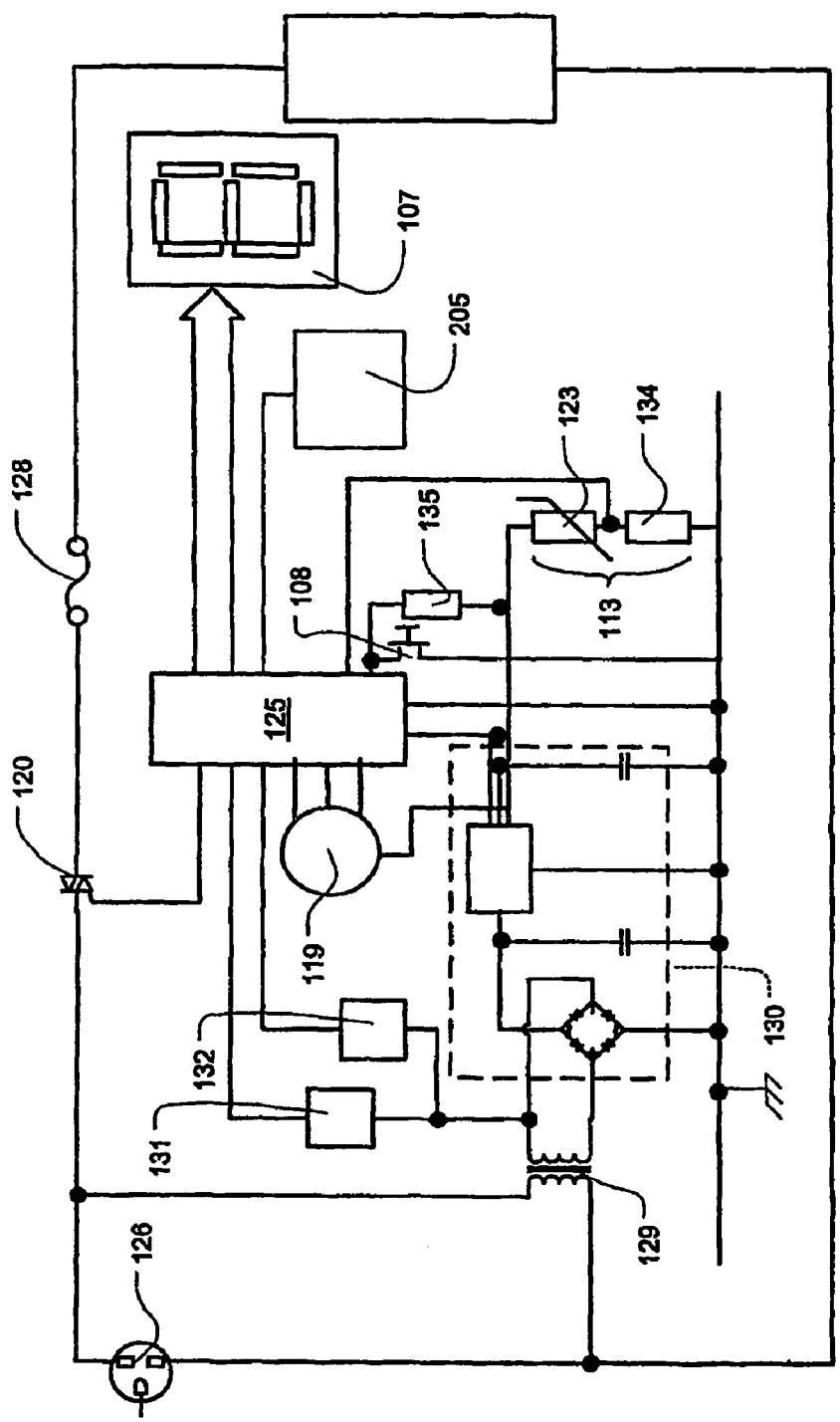
FIG. 29 is a block diagram of the control electronics of the bottle warmer of FIG. 28.

Referring to FIG. 29, die control circuit is the same as that of the first bottle warmer 101 described above except that an output of the microcontroller 125 is used to control the solenoid valve 205.

The operation of the second bottle warmer 201 is the same as the operation of the first bottle warmer 101 with the addition of the control of the solenoid value 205. Under normal circumstance, the solenoid valve 205 is closed. However, the microcontroller 125 outputs a signal to open it in step s140 so that the hot water can drain into the chamber 202.

It will be appreciated that many modifications may be made to the embodiments described above. For example, heating elements having different power and voltage ratings could be used. Additionally, a bottle warmer may use the same temperature control arrangements as the simplified steriliser.

The invention claimed is:

1. A babycare heating apparatus comprising:
a vessel for containing water;
a heating element for heating the water held in the vessel;
a temperature sensor for sensing a temperature rise effected by operation of the heating element; and
a controller configured to energize the heating element in response to an output of the temperature sensor,
wherein the controller is configured to de-energize the heating element if a change in the sensed temperature, sensed by the temperature sensor, meets a predetermined criterion including a first reference value and a second reference value, and
wherein the controller is further configured to compare the sensed temperature, at a predetermined time after energizing the heating element, with the first reference value and the second reference value, and de-energize the heating element if the sensed temperature is above the first reference value or below the second reference value, the controller being further configures to provide a first signal indicating that a level of the water in the vessel is low when the sensed temperature is above the first reference value, and to provide a second signal indicating that the vessel is overfilled with the water when the sensed temperature is below the second reference value.

2. The babycare heating apparatus according to claim 1, wherein the controller is further configured to determine a rate of change in the sensed temperature, sensed by the sensor, and compare said rate with the reference value, and wherein said criterion comprises said rate is greater than a threshold value.

3. The babycare heating apparatus according to claim 1, wherein the controller is further configured to determine a rate of change in the sensed temperature, sensed by the sensor, and compare said rate with the reference value, and wherein said criterion comprises said rate being less than a threshold value.

4. The babycare heating apparatus according to claim 1, wherein the controller is further configured to determine a rate of change in the sensed temperature, sensed by the sensor, and compare said rate with the reference value, and wherein said criterion comprises said rate is within a predetermined range.

5. The babycare heating apparatus according to claim 1, comprising a metallic heat conductor for conducting heat from the heating element to the water in the vessel.

6. The babycare heating apparatus according to claim 5, wherein the temperature sensor is arranged to sense the temperature of said conductor directly.

7. The babycare heating apparatus according to claim 1, wherein the vessel has a wall formed a from material that provides thermal protection for users.

8. The babycare heating apparatus according to claim 7, wherein the temperature sensor is mounted to a reduced thickness portion of said wall.

9. The babycare heating apparatus according to claim 8, wherein said reduced thickness portion has a thickness in the range of about 0.2 to about 1.0 mm.

10. The babycare heating apparatus according to claim 1, comprising a baby bottle warmer.

11. The babycare heating apparatus according to claim 1, comprising a sterilizer.

12. The babycare heating apparatus of claim 1, wherein the controller is further configured to perform a diagnostic test and provide an indication of readiness or error based on results of the diagnostic test, the diagnostic test including measuring mains voltage and frequency provided to the babycare heating apparatus.

13. The babycare heating apparatus of claim 12, wherein the controller is further configured to determine the mains voltage and frequency from outputs of a zero-crossing detector and a peak voltage detecting circuit, and saves the determined mains voltage and frequency.

14. The babycare heating apparatus of claim 12, wherein the controller is further configured to determine the mains voltage and frequency from outputs of a zero-crossing detector and a peak voltage detecting circuit, and uses the determined mains voltage and frequency to provide control pulses to turn on a triac.

15. A babycare bottle warmer comprising:
a vessel for containing water and receiving a feeding bottle to be warmed;
a chamber;
a conduit between the vessel and the chamber,
a valve for opening and closing the conduit;
a heating element for heating water held in the vessel; and
a controller configured to open the valve at the end of a bottle heating operation so that hot water in the vessel can be conducted to the chamber, wherein the controller is further configured to compare a temperature of the water, at a predetermined time after energizing the heating element, with a first reference value and a second reference value, and de-energize the heating element if the temperature is above the first reference value or below the second reference value, the controller being further configures to provide a first signal indicating that a level of the water in the vessel is low when the temperature is above the first reference value, and to provide a second signal indicating that the vessel is overfilled with the water when the temperature is below the second reference value.

16. The babycare bottle warmer of claim 15, wherein the controller is further configured to perform a diagnostic test and provide an indication of readiness or error based on results of the diagnostic test, the diagnostic test including measuring mains voltage and frequency provided to the babycare heating apparatus.

17. The babycare bottle warmer of claim 16, wherein the controller is further configured to determine the mains voltage and frequency from outputs of a zero-crossing detector and a peak voltage detecting circuit, and saves the determined mains voltage and frequency.

18. The babycare bottle warmer of claim 16, wherein the controller is further configured to determine the mains voltage and frequency from outputs of a zero-crossing detector and a peak voltage detecting circuit, and uses the determined mains voltage and frequency to provide control pulses to turn on a triac.

* * * * *